United States Patent
Patisteas et al.

(10) Patent No.: US 11,097,087 B2
(45) Date of Patent: Aug. 24, 2021

(54) ACCESS PORT LOCATOR AND METHODS OF USE THEREOF

(71) Applicant: Primo Medical Group, Inc., Stoughton, MA (US)

(72) Inventors: Andrea Patisteas, Rochester, MA (US); Steven J. Tallarida, Mansfield, MA (US); John M. Butziger, East Greenwich, RI (US)

(73) Assignee: PRIMO MEDICAL GROUP, INC., Stoughton, MA (US)

( * ) Notice: Subject to any disclaimer, the term of this patent is extended or adjusted under 35 U.S.C. 154(b) by 114 days.

(21) Appl. No.: 16/260,621

(22) Filed: Jan. 29, 2019

(65) Prior Publication Data

US 2019/0224465 A1 Jul. 25, 2019

Related U.S. Application Data

(63) Continuation of application No. 15/423,862, filed on Feb. 3, 2017, now Pat. No. 10,188,844.

(60) Provisional application No. 62/291,761, filed on Feb. 5, 2016, provisional application No. 62/359,397, filed on Jul. 7, 2016.

(51) Int. Cl.
 *A61M 39/02* (2006.01)

(52) U.S. Cl.
 CPC . *A61M 39/0208* (2013.01); *A61M 2039/0238* (2013.01)

(58) Field of Classification Search
 CPC .................. A61M 39/0208; A61M 2039/0238
 See application file for complete search history.

(56) References Cited

U.S. PATENT DOCUMENTS

| | | | | |
|---|---|---|---|---|
| 4,675,006 | A | * | 6/1987 | Hrushesky ............ A61M 25/02 128/DIG. 26 |
| 5,571,092 | A | * | 11/1996 | Thompson ........ A61M 39/0208 604/263 |
| 5,620,419 | A | | 4/1997 | Lui et al. |
| 10,188,844 | B2 | * | 1/2019 | Patisteas ........... A61M 39/0208 |
| 2004/0181240 | A1 | | 9/2004 | Tseng et al. |
| 2004/0220528 | A1 | | 11/2004 | Garcia, Jr. |
| 2006/0030825 | A1 | * | 2/2006 | Enns ...................... A61M 5/158 604/264 |
| 2009/0287132 | A1 | | 11/2009 | Vess |
| 2012/0123344 | A1 | | 5/2012 | Hornig et al. |
| 2013/0110053 | A1 | * | 5/2013 | Yoshino ................ A61J 1/1406 604/201 |

(Continued)

FOREIGN PATENT DOCUMENTS

EP 0255215 3/1988

OTHER PUBLICATIONS

International Search Report and Written Opinion dated Apr. 27, 2017, issued in PCT Patent Application No. PCT/US17/16398, 13 pages.

(Continued)

*Primary Examiner* — Theodore J Stigell
(74) *Attorney, Agent, or Firm* — Grossman, Tucker, Perreault & Pfleger, PLLC

(57) ABSTRACT

A method of treating a host having an implanted subcutaneous access port, comprising using an access port locater configured to locate a subcutaneous access port located beneath a skin surface of a host.

18 Claims, 7 Drawing Sheets

(56) References Cited

U.S. PATENT DOCUMENTS

2013/0204228 A1     8/2013   Smith et al.
2015/0320639 A1    11/2015   Perot et al.

OTHER PUBLICATIONS

Extended Search Report dated Oct. 1, 2019, issued in European Patent Application No. 17748225.4, 11 pages.

* cited by examiner

ACCESS PORT LOCATOR AND METHODS OF USE THEREOF

CROSS-REFERENCE TO RELATED APPLICATIONS

This application is a continuation of U.S. patent application Ser. No. 15/423,862 (now U.S. Pat. No. 10,188,844) filed Feb. 3, 2017, which claims the benefit of U.S. provisional patent application Ser. No. 62/291,761 filed Feb. 5, 2016 and U.S. provisional patent application Ser. No. 62/359,397 filed Jul. 7, 2016, the entire disclosures of which are incorporated herein by reference.

FIELD

The present disclosure relates to medical devices, and more particularly an access port locator.

BACKGROUND

Implanted subcutaneous access ports can be difficult to locate, isolate, grasp and target with needles during access, especially given the wide variety of port geometries in the market place. Problems that may occur during access include accidental needle sticks of the clinician's fingers, poor targeting resulting in a missed septum and/or punctured catheter. Additionally, the sealing quality of a port septum may be compromised by repeated access punctures in the same location, which can occur with current access methods given the difficulty of visualizing and recording the repeated port needle access locations.

U.S. Pat. No. 5,620,419 to Lui et al. discloses a noninvasive, perforate, self-centering locator which facilitates engagement of a needle or cannula with a subcutaneously implanted access port. The locator is exemplified by a port stabilizer ring having a central opening. During use, the stabilizer ring is pressed on the skin over the site of the port, and simultaneously visually locates the septum of the port for the user while stabilizing the port with respect to the skin and underlying tissues, permitting ready penetration of the skin and septum by the needle or cannula.

However, Lui does not provide for protection of the user of the locator against inadvertent sticks from the needle or cannula. Furthermore, the wide configuration of the ring of Lui makes it difficult to apply suitable pressure to the skin by the user to locate a port which may be deeply implanted in subcutaneous tissue. Moreover, Lui does not provide any means for determining and/or avoiding prior penetration locations of the port septum with the needle or cannula, which could expedite septum failure if the same penetration locations are used repeatedly.

SUMMARY

The present disclosure provides a medical device comprising an access port locater configured to locate a subcutaneous access port located beneath a skin surface of a host, which may particularly provide for protection of a user of the access port locator (e.g. a clinician) against inadvertent sticks from the needle or cannula, as well as aid in determining and/or avoiding prior penetration locations of the port septum with the needle or cannula.

In at least one embodiment, the present disclosure provides a medical device comprising an access port locater configured to locate a subcutaneous access port located beneath a skin surface of a host, with the access port locator including at least one annular ring having first and second opposing ends and a longitudinal access, the annular ring positionable on the skin surface of the host with the first end of the annular ring in contact with the skin surface and the longitudinal axis of the annular ring substantially perpendicular to the skin surface; at least one stabilizing flange configured to stabilize the access port locater on the skin surface; and at least one needle guard configured to shield a hand of a user of the access port locator when the hand is positioned on the stabilizing flange.

In at least one embodiment, a first end region at the first end of the annular ring forms an annular protrusion relative to the at least one stabilizing flange which is arranged to provide a pressure concentration ridge.

In at least one embodiment, the annular ring and the at least one stabilizing flange are arranged such that, when the at least one stabilizing flange is located on the skin surface, a first end region at the first end of the annular ring forms an annular protrusion arranged to press into the skin surface.

In at least one embodiment, the at least one stabilizing flange and the at least one needle guard are arranged such that a pocket is formed between the at least one stabilizing flange and the at least one needle guard to receive a digit of the hand of the user.

In at least one embodiment, the at least one stabilizing flange and the at least one needle guard are arranged such that, when the at least one stabilizing flange is located on the skin surface, the at least one needle guard overlies at least a portion of the at least one stabilizing flange.

In at least one embodiment, the at least one needle guard extends from the second end of the annular ring with an arcuate convex contour which curves away from the longitudinal axis of the annular ring.

In at least one embodiment, the at least one needle guard configured to shield the hand of the user when the hand is positioned on the at least one stabilizing flange comprises at least two needle guards to shield the hand of the user when the hand is positioned on the at least one stabilizing flange.

In at least one embodiment, the at least two needle guards are located on opposite sides of the annular ring.

In at least one embodiment, the at least two needle guards are substantially identical.

In at least one embodiment, the at least one stabilizing flange configured to stabilize the access port locater on the skin surface further comprises at least two stabilizing flanges configured to stabilize the access port locater on the skin surface.

In at least one embodiment, the at least two stabilizing flanges are located on opposite sides of the annular ring.

In at least one embodiment, a skin receiving gap is located between the at least two stabilizing flanges.

In at least one embodiment, the at least two stabilizing flanges are planar.

In at least one embodiment, the at least two stabilizing flanges are located in a common plane.

In at least one embodiment, the at least two stabilizing flanges are substantially parallel.

In at least one embodiment, the at least two stabilizing flanges are substantially identical.

In at least one embodiment, the at least one stabilizing flange extends outwardly from the annular ring.

In at least one embodiment, the at least one stabilizing flange extending outwardly from the annular ring is substantially perpendicular to the longitudinal access of the annular ring.

In at least one embodiment, the at least one stabilizing flange extending outward from the annular ring diverges away from the at least one needle guard as the at least one stabilizing flange extends outward from the annular ring.

In at least one embodiment, the at least one stabilizing flange extending outwardly from the annular ring is angled towards a bottom end of the access port locator.

In at least one embodiment, the annular ring is a closed annular ring.

In at least one embodiment, the annular ring is cylindrical.

In at least one embodiment, the annular protrusion is circular.

In at least one embodiment, the annular ring forms an aperture, and a membrane at least partially covers the aperture. The membrane may be coupled to the annular ring.

In at least one embodiment, the membrane is removably coupled to the annular ring by an adhesive, such as a pressure sensitive adhesive.

In at least one embodiment, the membrane includes at least one indicia indicative of and/or corresponding to one or more needle use locations of the access port.

In at least one embodiment, the annular ring is a split annular ring and may include a hinge.

In at least one embodiment, the access port locator is configured to mechanically engage with the subcutaneous access port, such as with an interference which inhibits separation of the access port locator from the access port.

In at least one embodiment, the at least one annular ring comprises a first annular ring and a second annular ring, and the membrane is retained between the first annular ring and the second annular ring. The first and second annular rings may be arranged as inner and outer annular rings, respectively, or arranged as upper and lower annular rings, respectively.

FIGURES

The above-mentioned and other features of this disclosure, and the manner of attaining them, will become more apparent and better understood by reference to the following description of embodiments described herein taken in conjunction with the accompanying drawings, wherein.

DETAILED DESCRIPTION

Figure 1:
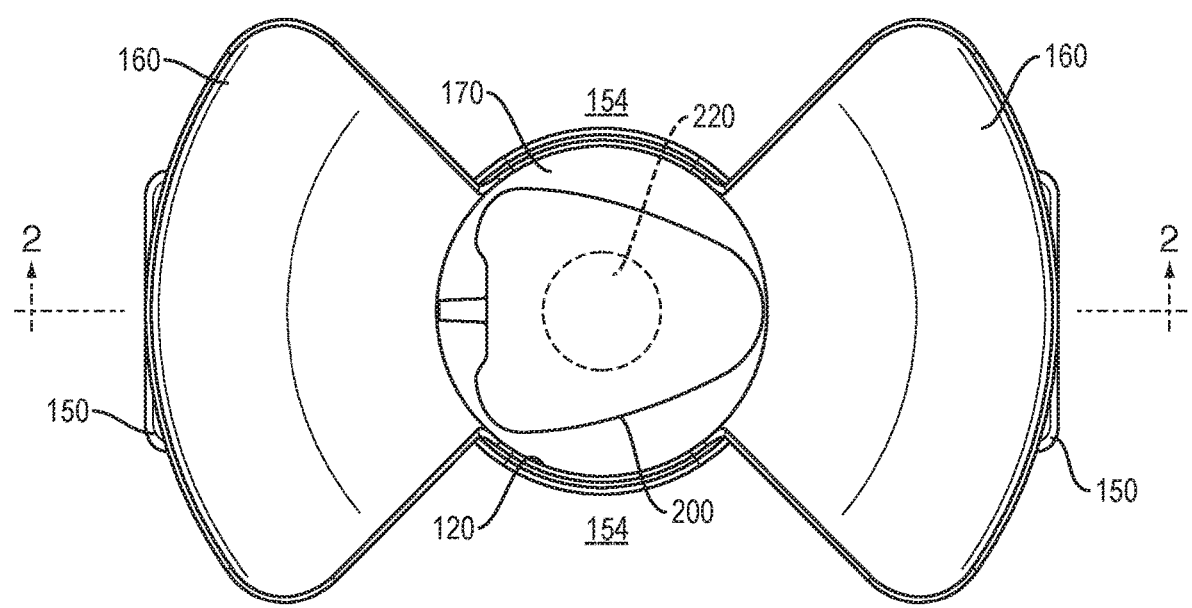
FIG. 1 is a top (plan) view of an access port locator according to the present disclosure.

It may be appreciated that the present disclosure is not limited in its application to the details of construction and the arrangement of components set forth in the following description or illustrated in the drawings. The invention(s) herein may be capable of other embodiments and of being practiced or being carried out in various ways. Also, it may be appreciated that the phraseology and terminology used herein is for the purpose of description and should not be regarded as limiting as such may be understood by one of skill in the art.

Figure 2:
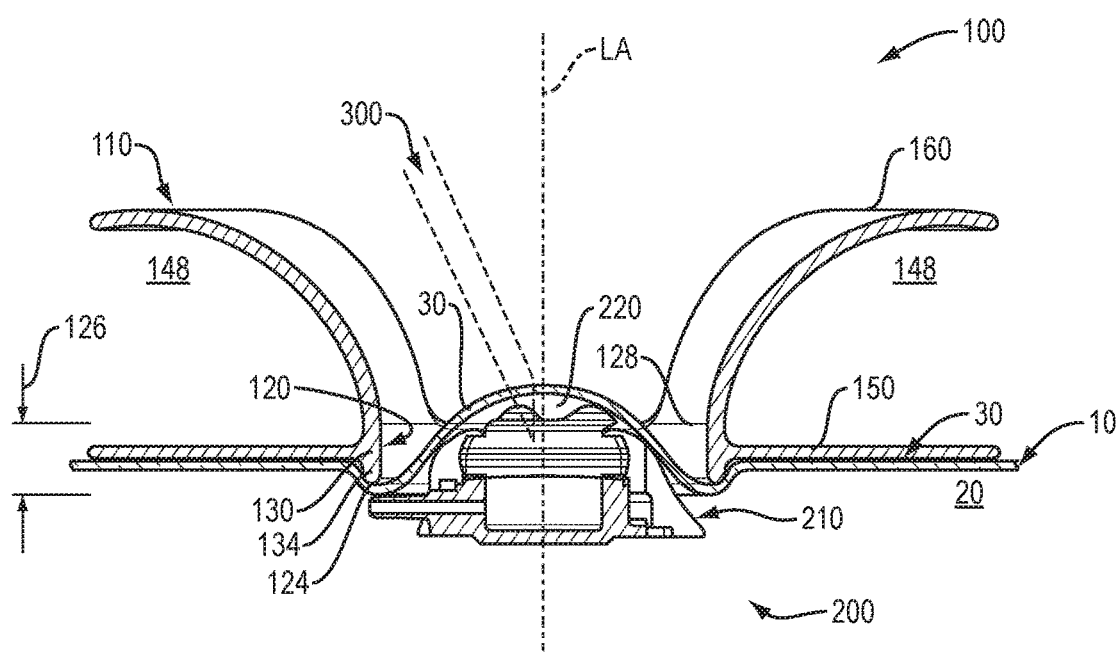
FIG. 2 is a cross-sectional side view of an access port locator of FIG. 1 taken along line 2-2.

Referring now to FIGS. 1-2, there is shown a medical device 100 comprising a non-invasive, self-centering, access port locator 110 engaging an implanted (subcutaneous) access port 200. The access port locator 110 may be useable, particularly a medical clinician, to visually locate the access port 200 when positioned within the skin/tissue 20 of a host 10, particularly beneath the skin surface 30. The access port locator 110 may also be used to retain the access port 10 and stabilize it against lateral movement during insertion of a tubular penetrating member 300 (e.g. needle) through the skin/tissue 20 and to the access port 200. The access port locator 110 may be formed of metal or plastic composition, such as rigid injection molded thermoplastic such as polypropylene.

The access port locator 110 includes an annular ring 120 having first and second opposing ends 124 and 128, respectively, and a longitudinal axis LA, which may also be understood as the longitudinal axis of the access port locator 110. While the annular ring 120 is shown as a closed, cylindrical annular ring, the annular ring 120 may also be in a form of a substantially closed split ring, and may not be cylindrical. For example, as referring to FIG. 3, there is shown an annular ring 120 as a split ring, with a split ring opening 122. As shown the split ring provides at least 75% of the circumference of a closed ring, and more particularly at least 85% of the circumference of a closed ring, and more particularly at least 95% of the circumference of a closed ring. The split ring 120 may also be a multi-piece configuration (as opposed to a single piece), with the side of the split ring 120 opposite the split ring opening 122 including a hinge 136 (e.g. spring-loaded piano hinge biased against opening of the ring 120) which allows rotation of opposing split ring halves 138a, 138b to increase and decrease the size of the split ring opening 122. When a needle 300 is introduced through the annular ring 120 and into host 10, a split ring 120 may enable a clinician to remove the access port locator 110 laterally without disturbing or otherwise removing the needle 300.

As shown, when positioned on the skin surface 30 of host 10, the first end 124 of the annular ring 120 is in contact with the skin surface 30 and the longitudinal axis LA of the annular ring 120 is substantially perpendicular (transverse) to the skin surface 30. As such, the annular ring 120 is further arranged with longitudinal length 126 between the first end 124 and second end 128 also substantially perpendicular (transverse) to the skin surface 30. As used herein, the longitudinal axis LA of the annular ring 120 may be understood to be substantially perpendicular (transverse) to the skin surface 30 when the longitudinal axis LA of the annular ring 120 is within 15 degrees of being perfectly perpendicular at 90 degrees to the skin surface 30.

The access port locator 110 further includes at least one stabilizing flange 150 configured to stabilize the access port locater 110 on the skin surface 30. More particularly, as shown, at least two opposing planar stabilizing flanges 150 (on opposite outer sides of the annular ring 120 extend outwardly (laterally) from the annular ring 120 substantially perpendicular (transverse) to the longitudinal access LA of the annular ring 120. Similarly, the at least two opposing stabilizing flanges 150 may be understood to be substantially perpendicular (transverse) to the longitudinal access LA of the annular ring 120 when the stabilizing flanges 150 are within 15 degrees of being perfectly perpendicular at 90 degrees to the longitudinal access LA of the annular ring 120. The at least two opposing stabilizing flanges 150 may also be understood to be located in a common plane and substantially parallel to one another, as well as substantially identical mirror images.

The stabilizing flanges 150 are longitudinally off-set (axially spaced) from the first end 124 of annular ring 120, and intersect a medial region 130 of the annular ring 120. As shown, a first end region 134 at the first end 124 of the annular ring 120 forms an annular (circular) protrusion relative to the stabilizing flanges 150 which is arranged to provide a pressure concentration ridge. In such manner, the annular ring 120 and the stabilizing flanges 150 are arranged such that, when the stabilizing flanges 150 are located on the skin surface 30, the first end region 124 at the first end 124 of the annular ring 120 will press into the skin surface 30, thus facilitating location, as well as lateral stabilization, of the access port 200. Furthermore, pressure placed on the stabilizing flanges 150 by a hand of the clinician may be concentrated in the first end region 134 to depress the skin/tissue 20 and aid in location and lateral stabilization of the access port 200.

As shown by FIG. 2, skin receiving gaps 154 are located between the stabilizing flanges 150. When holding pressure is applied to the stabilizing flanges 150 and the skin/tissue 20 is depressed, the skin/tissue 20 between the stabilizing flanges 150 may rise above the plane of the stabilizing flanges 150 into the skin receiving gaps 154. In such manner, the skin/tissue 20 provides an anti-rotation mechanism to inhibit inadvertent rotation of the access port locator 110.

The access port locator 110 further includes at least one needle guard 160 configured to shield a hand of the clinician when the hand is positioned on a stabilizing flange 150. More particularly, as shown, at least two opposing needle guards 160, which are substantially identical mirror images, are arranged on opposite outer sides of the annular ring 120. As best shown by FIG. 1, the needle guards 160 extend from the second end 128 of the annular ring 120 with an arcuate convex contour which curves away from the longitudinal axis LA of the annular ring 120.

To provide orientation, particularly relative to the longitudinal axis LA, with the arrangement of the access port locator 110 as shown in FIG. 2, the needle guards 160 may be understood as being located at a top side 112 of the access port locator 100, while the portion of the access port locator 110 which interacts with the host 10 may be understood to be located at a bottom side of the access port locator 110. Furthermore, the split ring opening 122 may be understood to be located on a front side, while the opposite side may be understood to be the rear side.

The stabilizing flanges 150 and needle guards 160 are arranged such that pockets 148 are formed between the stabilizing flanges 150 and the needle guards 160 to each receive one or more digits (e.g. thumb, forefinger, index finger) of the hand of the clinician. More particularly, as best shown by FIG. 2, the stabilizing flanges 150 and needle guards 160 are aligned radially outward from the annual ring 120 such that, when the stabilizing flanges are located on the skin surface 30, the needle guards overlie a substantial portion, if not all, of the stabilizing flanges 150. As shown by FIG. 2, the needle guards 160 are radially wider than the stabilizing flanges 150. In such manner, a clinician placing their hand, and more particularly digits thereof, on the stabilizing flanges 150 to hold the access port locator 110 in place is less apt to be subject to a needle stick from a needle 300 being inserted into the access port 200 due to the needle guards 160 shielding the hand from above.

As shown by FIGS. 1 and 2, when the access port locator 110 is properly seated and pressed on skin/tissue 20, the access port 200 and the overlying skin/tissue may rise into and enter the center aperture 170 defined by annular ring 120, to delineate the position of the access port 200, and hold the access port 200 particularly from lateral movement.

In certain embodiments the access port 200 may have an access port body 210 body may be attracted to one another, particularly by magnetic force. In such regard, the access port 200 may have an access port body 210 body particularly formed of a magnetic composition, such as a magnetic polymer composition, in which case the polymer composition may comprise polymer (e.g. polyamide (nylon), polyphenylene sulfide) blended with a magnetic material (e.g. powder) such as ferrite, neodymium-iron-boron (NdFeB) and/or samarium cobalt (SmCo). In such embodiments, the access port locator 100 may also be formed of same materials and additionally have been formed into a permanent magnet. The access port locator 100 may also be formed of a non-metallic magnet made from an organic polymer, such as PANiCNQ, which is a combination of emeraldine-based polyaniline (PANi) and tetracyanoquinodimethane (TCNQ). Alternatively, the access port body 210 may be formed of a magnet, and the access port locator 100 may be formed of a magnetic material. Also alternatively, the access port body 210 and the access port locator 100 may each be permanent magnets having attracting (opposite) magnetic poles.

Figure 4:
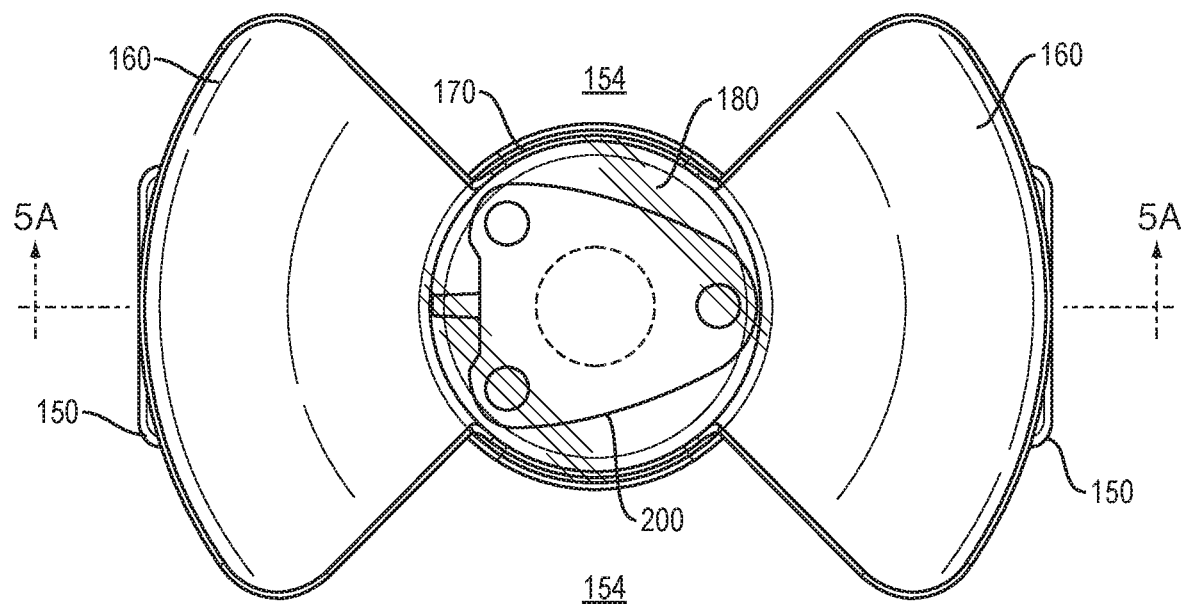
FIG. 4 is a top (plan) view of an access port locator of FIG. 1 further including a membrane extending over an aperture of an annular ring of the access port locator.
Figure 5A:
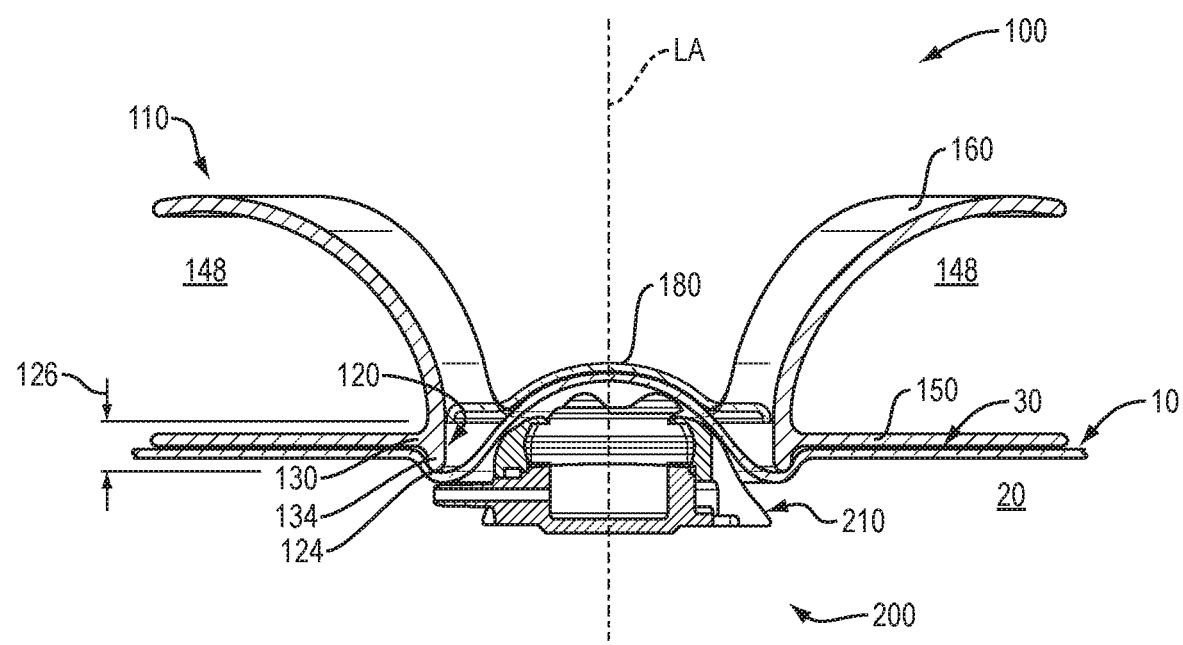
FIG. 5A is a cross-sectional side view of an access port locator of FIG. 4 taken along line 5A-5A.

As shown in FIGS. 4 and 5A, a stretchable (elastomeric) membrane 180 may be coupled to the annular ring 120 which at least partially or fully covers the center aperture 170. Membrane 180 may be used to inhibit blood or other bodily fluid splatter from arising during insertion or removal of a needle 300 through skin/tissue 20 and into access port 200. Membrane 180 may also include an anti-microbial coating or impregnation or layer that resists infection from foreign bodies entering the puncture site or migrating deeper from the skin 20. The membrane 180 may be temporarily adhesively bonded to the annular ring 120 with a pressure sensitive (tacky) adhesive which allows the membrane 180 to be peeled away or otherwise removed from the annular ring 120. After penetration of the membrane 170 by a needle 300, in a case where the annular ring 120 is a split ring, the membrane 180 may be unpeeled from the annular ring 120, and the access port locator 110 subsequently removed from the treatment site while the needle 300 is still inserted in the patient. The membrane 170 may then be adhesively bonded to the host 10 with a pressure sensitive adhesive located on the skin surface facing side of the membrane 170. In such regard, the membrane 170 may provide a temporary bandage after the needle 300 is withdrawn.

Figure 5B:
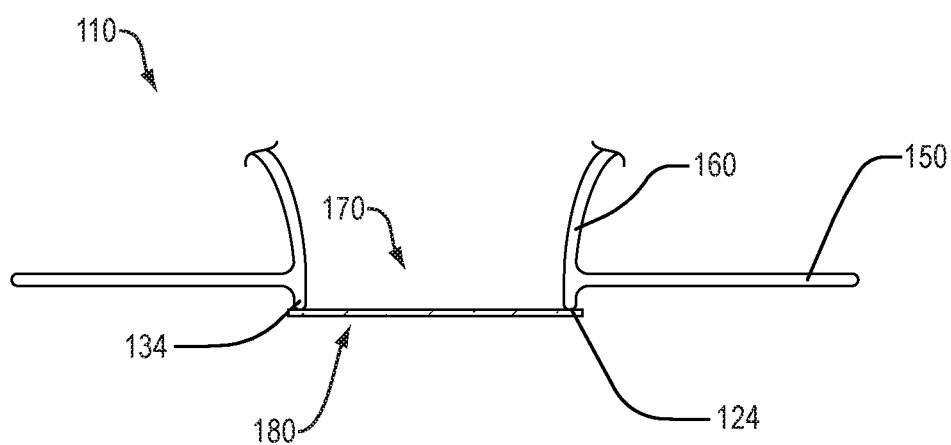
FIG. 5B is a cross-sectional side view of an access port locator including a membrane coupled to the annular ring.
Figure 5C:
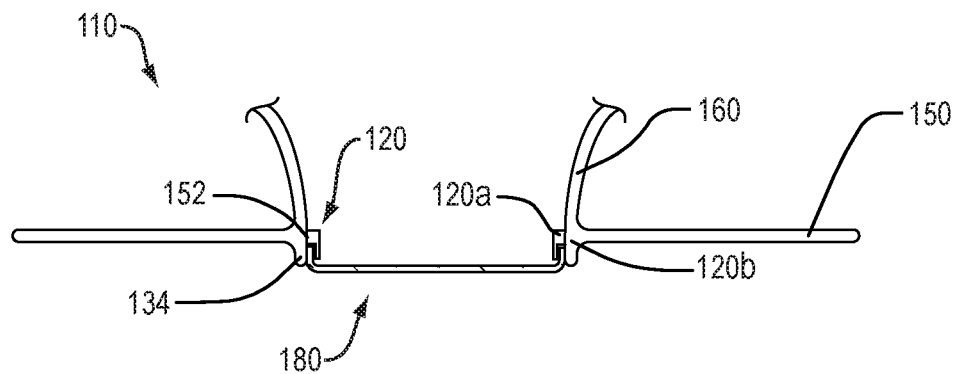
FIG. 5C is a cross-sectional side view of an access port locator including a membrane coupled between an inner annular ring and an outer annular ring.

Referring now to FIGS. 5A-5C, there are shown various configurations to couple the membrane 180 to the remainder of the access port locator 110. In FIG. 5B, the membrane 180 may be adhesively coupled to the first end 124 of the annular ring 120, particularly with a pressure sensitive adhesive or other adhesive on the side of the membrane facing away from the skin surface 30. Membrane 180 may also be permanently bonded to the first end 124 of the annular ring 120 such, such as by being welded thereto.

In FIG. 5C, annular ring 120 may further comprise an inner annular ring 120a and an outer annular ring 120b, with the membrane 180 being captured (e.g. friction (interference) fit, pinched or otherwise compressed) between the two concentric annular rings 120a, 120b. Membrane 180 may be permanently coupled between the two annular rings 120a, 120b or removeably coupled between the two annular rings 120a, 120b, depending on the strength of the friction fit. The inner ring 120a may be press fit within outer ring 120b, or the rings 120, 120b may be welded together a weld location 152.

Figure 5D:
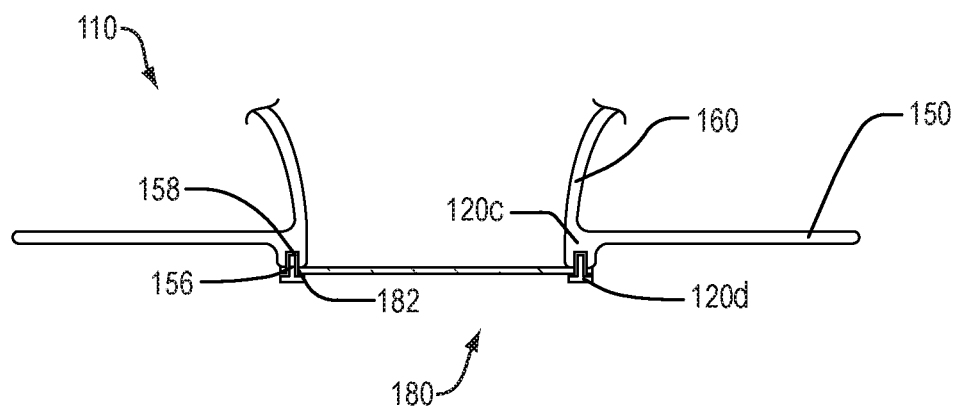
FIG. 5D is a cross-sectional side view of an access port locator including a membrane coupled between an upper annular ring and a lower annular ring.

In FIG. 5D, annular ring 120 may further comprise an upper annular ring 120c and a lower annular ring 120d, with the membrane 180 being captured (e.g. friction (interference) fit, pinched or otherwise compressed) between the two annular rings 120c, 120d. Membrane 180 may be permanently coupled between the two annular rings 120c, 120d or removeably coupled between the two annular rings 120c, 120d, depending on the strength of the friction fit. As shown, the lower ring 120d may include a plurality of posts 156 which extend through apertures 182 formed in membrane 180 and engage in post receptacles 158 formed on the upper ring 120c to positively mechanically engage with the membrane 180.

Figure 6:
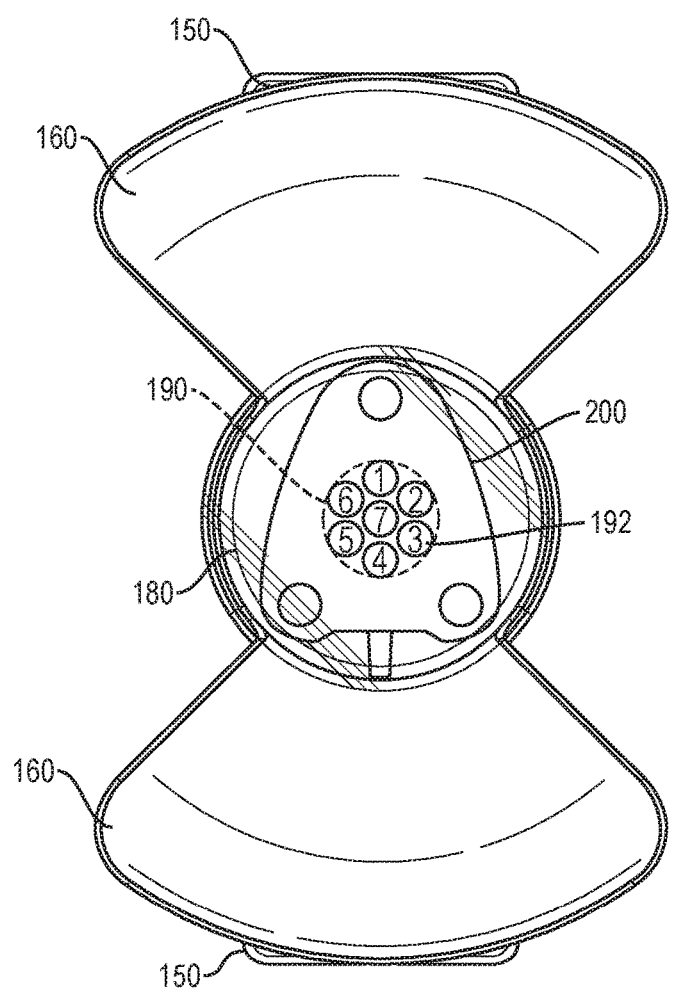
FIG. 6 is a top (plan) view of an access port locator of FIG. 4 with the membrane including at least one indicia indicative of and/or corresponding to one or more needle use locations of the access port.

As shown in FIG. 6, the membrane 180 may include a septum locator 190 (e.g. bullseye ring target area) to locate a septum 220, including the size and shape (geometry), within the access port body 210 of the access port, and/or an indicia 192 indicative of and/or corresponding to one or more needle use locations of the access port 200. The septum locator 190 and/or the indicia 192 may be printed or embossed on the membrane 180.

The septum locator 190/indicia 192 may comprise a depiction or image of the underlying port 200 to assist in visualizing the underlying port 200 in both size, shape, target area and geometry. This image could be indexed via the positioning of the annular ring 120 relative to the shape of the access port body 210. The image may also serve to visualize the location of the needle stick relative to the septum 210, which aids in recording the stick location so that site access variation can be more accurate and effective. As shown in FIG. 6, a puncture location grid or circles or other visual aids are printed along with the access port image to locate and identify the septum puncture location via a numbering system that identifies the needle stick region.

The diameter of the annular ring 120, which is significantly larger than the underlying port 200, also allows for fixation and grasping well outside the port perimeter such that it reduces the risk of needle sticks by widening the proximity of the clinician's fingers to the needle target area.

While shown as being perfectly circular with a constant diameter, the annular ring 120 of the access port locator 110 may have different shapes and sizes to access the various port sizes and shapes that exist in the market place. In some designs, the annular ring 120 of the access port locator 110 may match an outer shape of the access port body 210.

Figure 3:
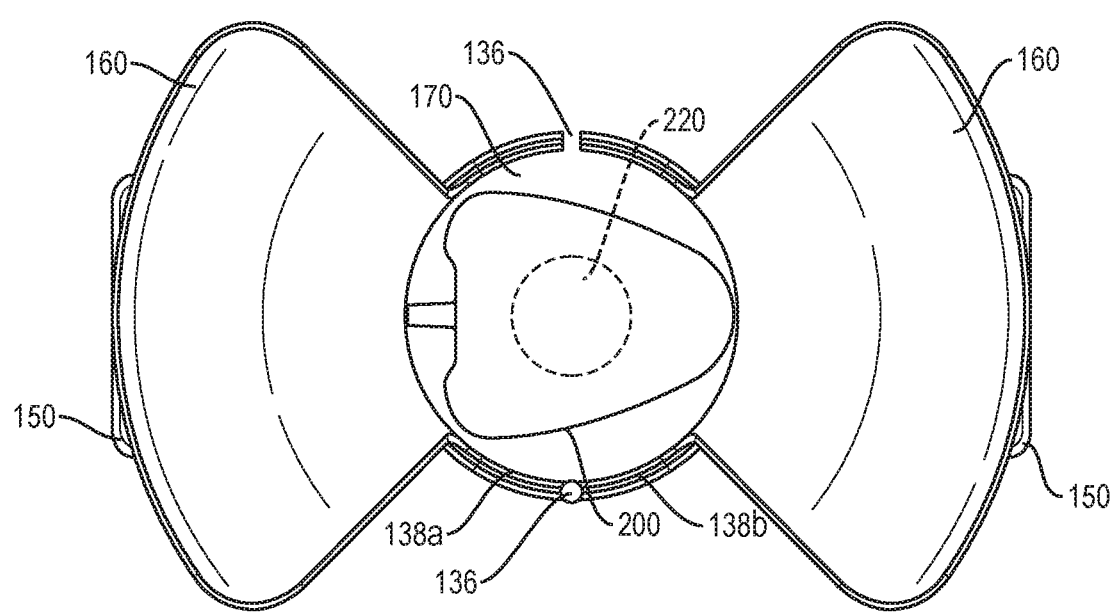
FIG. 3 is a top (plan) view of an access port locator of FIG. 1 further including a split ring.
Figure 7:
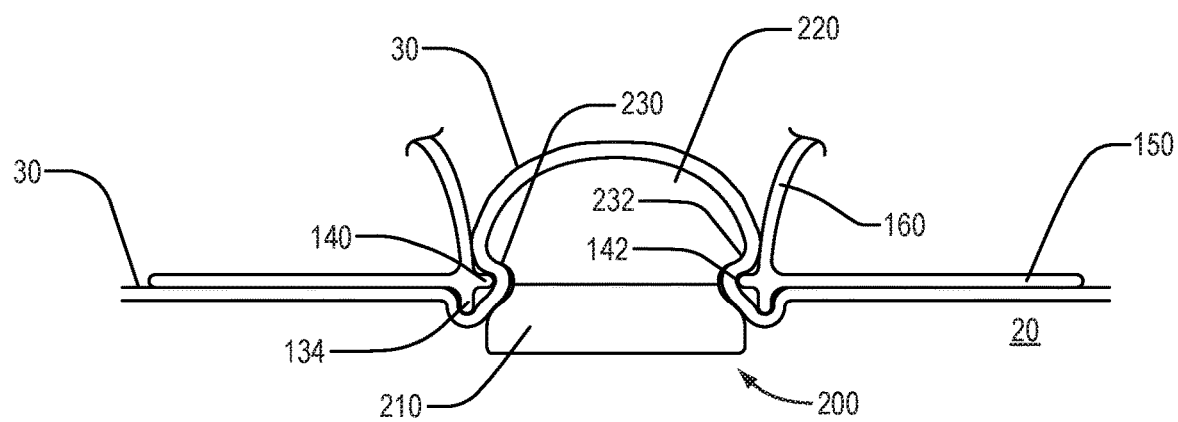
FIG. 7 is a cross-sectional side view of another access port locator according to the present disclosure.

Referring now to FIG. 7, there is shown the access port locator 110 of FIG. 3 further including at least one coupling engagement member 140 to positively mechanically couple with access port 200. As shown, the coupling engagement member 140 is in the form of a circular protrusion lip, which extends inwardly (laterally) from the annular ring 120 substantially perpendicular (transverse) to the longitudinal access LA of the annular ring 120. The coupling engagement member 140 may be understood to be substantially perpendicular (transverse) to the longitudinal access LA of the annular ring 120 when the coupling engagement member 140 is within 15 degrees of being perfectly perpendicular at 90 degrees to the longitudinal access LA of the annular ring 120. The coupling engagement member 140 may also be in a common plane and substantially parallel to the stabilizing flanges 150.

As shown in FIG. 7, the access port 200 further comprises at least one coupling engagement member 230 to form a mating positive mechanical engagement with coupling member 140 of access port locator 110. As shown coupling member 230 is in the form of a circular recess which extends around the longitudinal axis LA of the access port 200. As shown, the circular recess may be formed in the access port body 210 and/or the access port septum 220.

During use of the access port locator 110 of FIG. 7, the diameter of ring aperture 170 of the split annular ring 120 may first be increased by opening/expanding the split annular ring 120 via hinge 136 (see FIG. 3). The ring aperture 170 of the split annular ring 120 may be opened such that the inner edge 142 of the coupling member 140 will pass over the engagement shoulder 232 of the access port 200 when the access port locator 110 is pressed onto the skin/tissue 20, causing the skin/tissue 20, as well as the underlying access port 200 to enter ring aperture 170.

Thereafter, once the coupling engagement member 140 of the access port locator 110 (shown as the circular protrusion lip) is laterally aligned with coupling engagement member 140 of the access port 200 (shown as the circular recess to receive the circular protrusion lip) the ring aperture 170 of the split annular ring 120 may be closed/contracted such that at least a portion of the coupling engagement member 140 enters coupling engagement member 230 of the access port 200 (along with skin/tissue 20 located therebetween). As set forth herein, opening of hinge 136 may be biased by a spring, in which case closing of the hinge 136 may be performed by the bias force of the spring.

Once a portion of the coupling engagement member 140 of the access port locator 110 enters the coupling engagement member 230 of the access port 200, the access port locator 110 and the access port 200 are inhibited from separation along the longitudinal axis LA by the mechanical interference of the portion of the coupling engagement member 140 of the access port locator 110 within the coupling engagement member 230 of the access port 200 contacting against engagement shoulder 232 of the access port 200. Furthermore, the access port locator 110 and the access port 200 may be habited from axial separation by the compression/interference of the skin/tissue 20 between the coupling engagement member 140 of the access port locator 110 and the coupling engagement member 230 of the access port 200.

In the foregoing manner, once the access port locator 110 is positively mechanically coupled to the access port 200, it may be possible for a clinician to remove their hand from the access port locator 110 without the access port locator 110 losing a grasp of the access port 200 and the location of the access port 200. In order to remove the access port locator 110, the diameter of ring aperture 170 of the split annular ring 120 may be increased again by opening/expanding the split annular ring 120 via hinge 136.

Referring to FIGS. 8A-8D, there is shown another embodiment of an access port locator 110 according to the present disclosure. As shown, the stabilizing flanges 150 diverge away from the needle guards 160 as the stabilizing flanges extend away from the annular ring 120. More particularly, the stabilizing flanges are shown at an acute angle A of 60-85 degrees relative to the longitudinal axis LA and towards the first (bottom) end 124 of the access port locator 110, particularly annular ring 120, and skin surface 30, particularly for better skin gripping. Also, the split ring provides 75% to 90% of the circumference of a closed annular ring 120.

Also as shown, rather than the stabilizing flanges 150 and the needle guards 160 being equally (symmetrically) spaced around the longitudinal axis LA and annular ring 120 relative to the front side 116 and rear side 118 of the access port locator 110, the stabilizing flanges 150 and the needle guards 160 are closer towards the rear side 118 of the access port locator 110 and the front side 116 of the access port locator 110. In such manner, the stabilizing flanges 150 and the needle guards 160 may fit better in the V-shaped spaced formed between the index and middle digits (fingers) of a clinician.

Figure 8A:
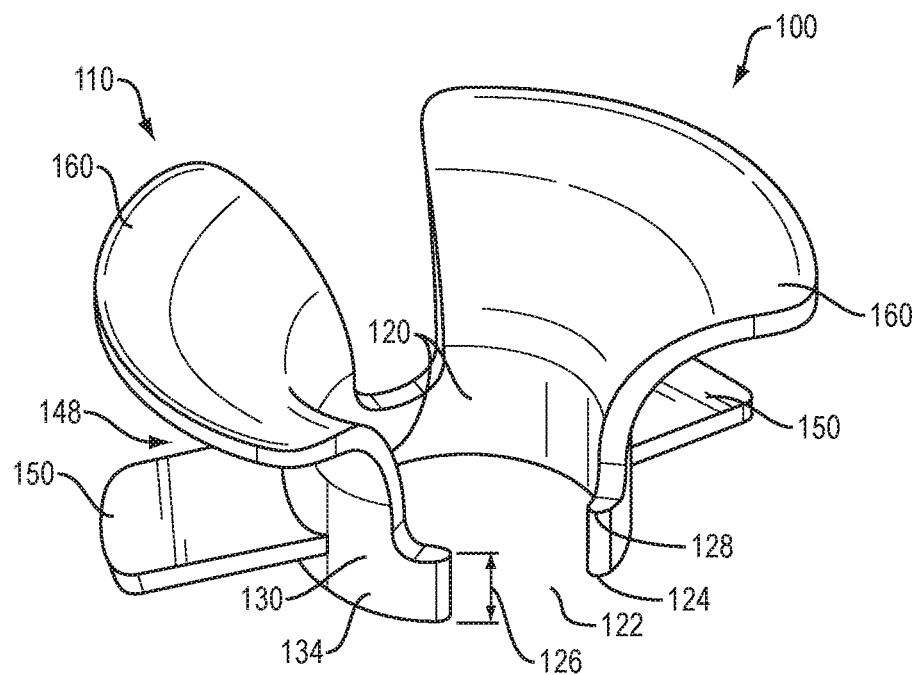
FIG. 8A is a perspective view of another access port locator according to the present disclosure.
Figure 8B:
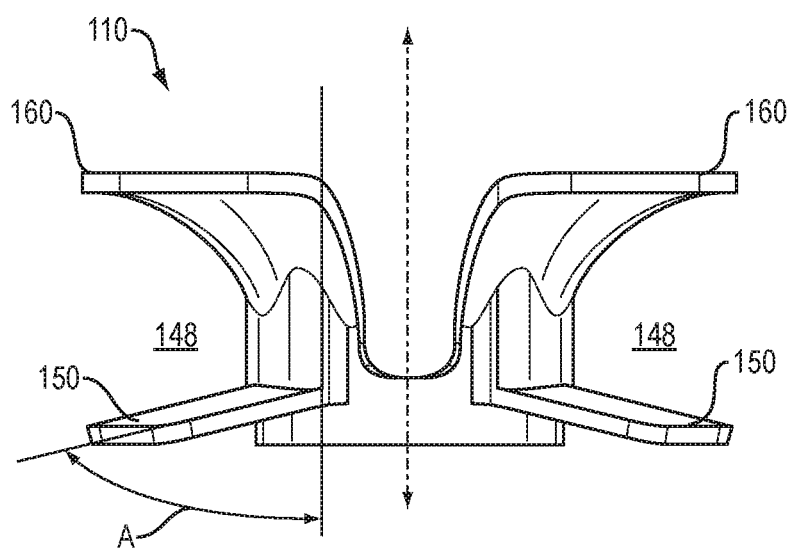
FIG. 8B is a side view of the access port locator of FIG. 8A.
Figure 8C:
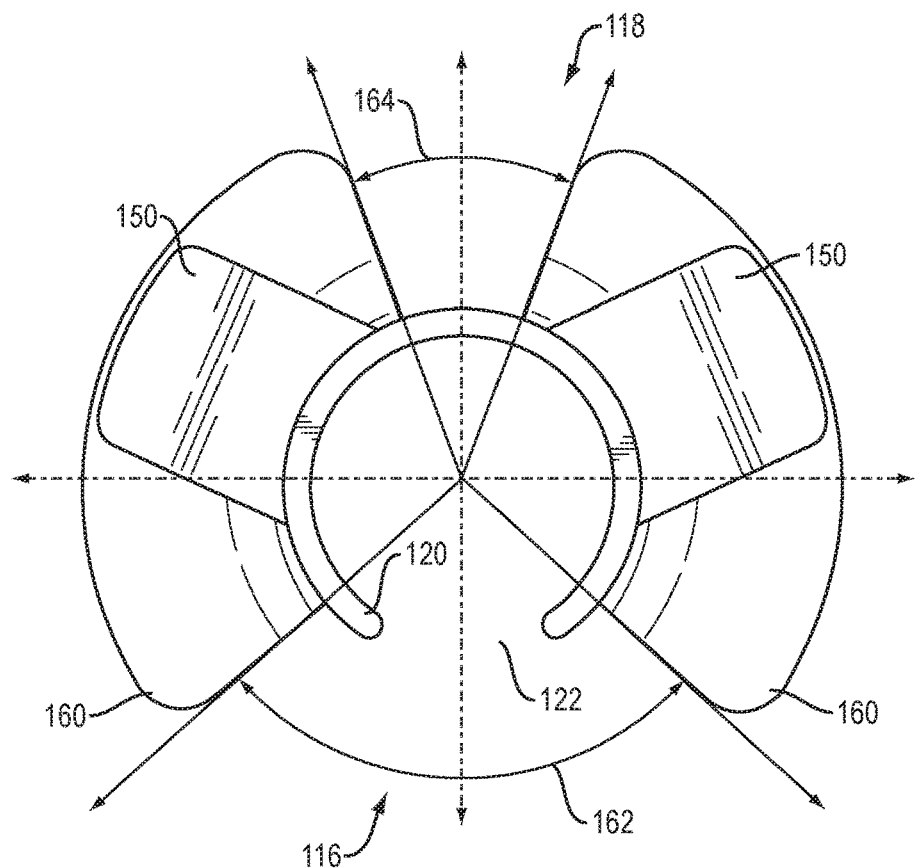
FIG. 8C is a first bottom view of the access port locator of FIG. 8A.

As shown by FIG. 8C, as indicated by small width of the rear needle guard gap 164 at the rear side 118 of the access port locator 110 as compared to the larger width of the front needle guard gap 162 at the front side 116 of the access port locator 110, the needle guards 160 are closer together towards the rear side 118 of the access port locator 110 than the front side 116 of the access port locator 110.

Figure 8D:
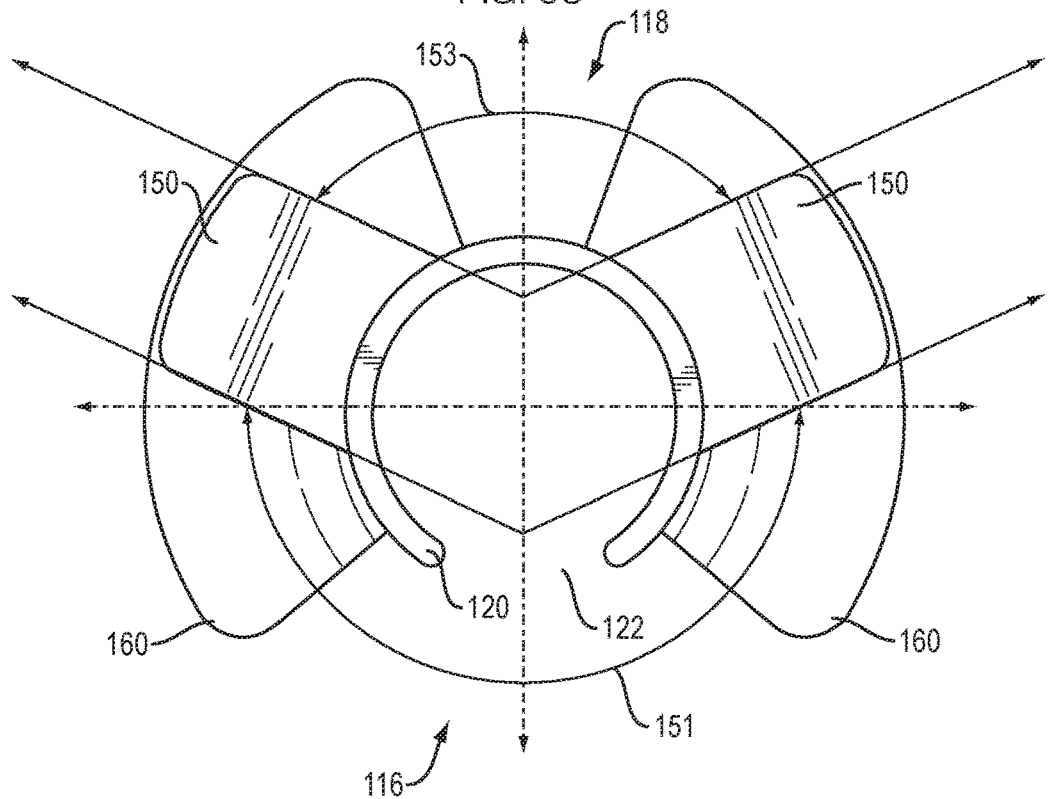
FIG. 8D is a second bottom view of the access port locator of FIG. 8A.

Similarly, as shown by FIG. 8D, as indicated by small width of the rear stabilizing flange gap 153 at the rear side 118 of the access port locator 110 as compared to the larger width of the front stabilizing gap 151 at the front side 116 of the access port locator 110, the stabilizer flanges 150 are closer together towards the rear side 118 of the access port locator 110 than the front side 116 of the access port locator 110.

While a preferred embodiment of the present invention(s) has been described, it should be understood that various changes, adaptations and modifications can be made therein without departing from the spirit of the invention(s) and the scope of the appended claims. The scope of the invention(s) should, therefore, be determined not with reference to the above description, but instead should be determined with reference to the appended claims along with their full scope of equivalents. Furthermore, it should be understood that the appended claims do not necessarily comprise the broadest scope of the invention(s) which the applicant is entitled to claim, or the only manner(s) in which the invention(s) may be claimed, or that all recited features are necessary.

LIST OF REFERENCE CHARACTERS 10 host
20 skin/tissue
30 skin surface
100 medical device
110 access port locator
112 top side
114 bottom side
116 front side
118 rear side
120 annular ring
120a inner annular ring
120b outer annular ring
122 split ring opening
124 first end of annular ring
126 ring length
128 second end of annular ring
130 medial region
134 first end region
136 hinge
138 split ring halves 138a, 138b
140 coupling engagement member
142 inner edge of coupling member
148 pocket
150 stabilizing flange(s)
151 front stabilizing flange gap
152 welds
153 rear stabilizing flange gap
154 skin receiving gap
156 post
158 post receptacle
160 needle guard
162 front needle guard gap
164 rear needle guard gap
170 ring aperture
180 membrane
182 membrane apertures
190 septum locator
192 indicia
200 access port
210 access port body
212 chamber
220 access port septum
230 coupling engagement member
232 engagement shoulder
300 tubular penetrating member/needle
A angle
LA longitudinal axis

What is claimed is:

1. A method of treating a host having an implanted subcutaneous access port, comprising:
using an access port locater configured to locate a subcutaneous access port located beneath a skin surface of a host, the access port locator including
at least one annular ring forming an aperture, the at least one annular ring having a longitudinal ring length disposed between first and second opposing ends, the at least one annular ring positionable on the skin surface of the host with the first end of the at least one annular ring in contact with the skin surface;
at least one stabilizing flange configured to stabilize the access port locater on the skin surface, the at least one stabilizing flange extending laterally from the longitudinal ring length of the at least one annular ring;
at least one needle guard configured to shield a hand of a user of the access port locator when the hand is positioned on the at least one stabilizing flange;
a first end region at the first end of the at least one annular ring forms an annular protrusion relative to the at least one stabilizing flange which is arranged to provide a pressure concentration ridge to press into the skin surface; and
the annular protrusion disposed adjacent the aperture; and
positioning the access port locator on the skin surface of the host with the implanted subcutaneous access port disposed within the aperture of the access port locator and the first end of the at least one annular ring in contact with the skin surface.

2. The method of claim 1, further comprising:
stabilizing the access port locater on the skin surface with the at least one stabilizing flange.

3. The method of claim 1, further comprising:
shielding the hand of the user of the access port locator with the at least one needle guard when the hand is positioned on the at least one stabilizing flange.

4. The method of claim 1, wherein:
the at least one stabilizing flange and the at least one needle guard are arranged such that a pocket is formed between the at least one stabilizing flange and the at least one needle guard; and
placing a digit of the hand of the user in the pocket when the hand is positioned on the at least one stabilizing flange.

5. The method of claim 1, further comprising:
pressing the access port locator into the host with the annular protrusion providing a pressure concentration ridge.

6. The method of claim 1, further comprising:
inserting a needle through the aperture of the access port locator into the host and into the implanted access port.

7. The method of claim 6, wherein:
the access port locator further comprises a membrane which at least partially covers the aperture; and
inserting the needle through the aperture of the access port locator into the host and into the implanted access port further comprises inserting the needle through the membrane.

8. The method of claim 7, wherein:
the membrane is coupled to the at least one annular ring.

9. The method of claim 8, wherein:
the membrane is removably coupled to the at least one annular ring by an adhesive.

10. The method of claim 7, wherein:
the membrane includes at least one indicia indicative of and/or corresponding to one or more needle access locations of the access port; and
inserting the needle through the membrane further includes inserting the needle through the membrane using the at least one indicia to locate an access location of the access port.

11. The method of claim 1, wherein:
the at least one stabilizing flange and the at least one needle guard are arranged such that, when the at least one stabilizing flange is located on the skin surface, the at least one needle guard overlies at least a portion of the at least one stabilizing flange.

12. The method of claim 1, wherein:
the at least one needle guard configured to shield the hand of the user when the hand is positioned on the at least one stabilizing flange comprises at least two needle guards to shield the hand of the user when the hand is positioned on the at least one stabilizing flange.

13. The method of claim 1, wherein:
the at least one stabilizing flange configured to stabilize the access port locater on the skin surface further comprises at least two stabilizing flanges configured to stabilize the access port locater on the skin surface.

14. The method of claim 1, wherein:
the at least one annular ring is a closed annular ring.

15. The method of claim 1, wherein:
the at least one annular ring is a split annular ring.

16. The method of claim 1, wherein:
the annular protrusion is circular.

17. The method of claim 1, wherein:
the access port locator is configured to mechanically engage with the subcutaneous access port.

18. The method of claim 17, wherein:
the access port locator is configured to mechanically engage with the subcutaneous access port with an interference which inhibits separation of the access port locator from the access port.

* * * * *